United States Patent [19]

Utsunomiya et al.

[11] Patent Number: 5,008,401

[45] Date of Patent: Apr. 16, 1991

[54] CYANINE COMPOUNDS

[75] Inventors: Masayuki Utsunomiya, Ashiya; Shigeo Fujita, Kawachinagano; Toshiyuki Nozawa, Sakai; Morihiro Kamiyama, Ibaraki, all of Japan

[73] Assignee: Asahi Chemical Co., Ltd., Osaka, Japan

[21] Appl. No.: 509,830

[22] Filed: Apr. 17, 1990

[51] Int. Cl.$^5$ ............................................. C07D 403/06
[52] U.S. Cl. .................................................... 548/455
[58] Field of Search ........................................ 548/455

[56] References Cited

U.S. PATENT DOCUMENTS

| | | | |
|---|---|---|---|
| 1,524,791 | 2/1925 | Konig | 548/455 |
| 1,863,679 | 6/1932 | Wahl | 548/455 |
| 3,592,653 | 7/1971 | Fumia, Jr. et al. | 96/101 |
| 3,916,069 | 10/1975 | Tiers et al. | 428/411 |
| 3,974,147 | 8/1976 | Tiers et al. | 260/240 |
| 4,025,347 | 5/1977 | Beretta et al. | 96/101 |
| 4,600,625 | 7/1986 | Abe et al. | 428/167 |
| 4,847,385 | 7/1989 | Kusakata et al. | 548/455 |

Primary Examiner—David B. Springer
Attorney, Agent, or Firm—Armstrong, Nikaido, Marmelstein, Kubovcik & Murray

[57] ABSTRACT

This invention relates to a cyanine compound represented by the formula (1)

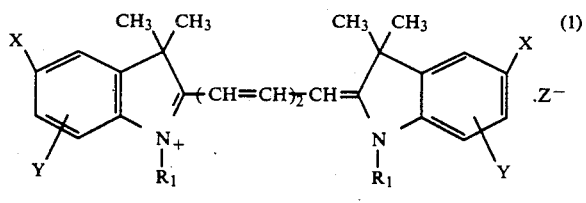

wherein:
X is a lower alkoxy, Y is a lower alkyl or a lower alkoxy, $R_1$ is a lower alkyl, or a lower alkyl substituted with at least one of $C_1$–$C_4$ alkoxy, hydroxy, sulfo, carboxy, $C_1$–$C_4$ alkyl amino, acetoxy, $C_1$–$C_4$ alkoxy carbonyl, $C_1$–$C_4$ sodium sulfonate, $C_1$–$C_4$ sodium carboxylate, alkyl amino methyl, acetoxy methyl, and methoxyl carbonyl methyl, and $Z^-$ is an anion.

5 Claims, No Drawings

CYANINE COMPOUNDS

The present invention relates to novel cyanine compounds.

Prevalently used among inorganic recording media for semiconductor laser recording are those containing a predominant amount of tellurium for forming a recording layer. Tellurium-type materials, however, have the drawbacks of being toxic, low in corrosion resistance, expensive and unfit to densify. Research is under way to develop organic dyes which can replace the inorganic tellurium-type materials.

Given below are important characterisitics required of organic dyes useful as recording media:

(1) properties of absorbing a suitable amount of near infrared light at a short wavelength, e.g. approximately 700 to 900 nm and undergoing fusion in order to provide a desired recording density and a suitable signal-to-noise ratio, sublimation, decomposition and like changes by exposure to the action of heat energy;

(2) desirable ability to reflect intensely the light for detection of signals in reproduction;

(3) good solubility in a solvent such as methanol or like alcohol which is unlikely to erode substrates made of polycarbonate, an acrylic resin or like synthetic resin, in view of need for formation of a recording layer by wet coating method;

(4) an ability to give records having a highly stable shape retention and an excellent retentivity, more specifically for 10 years or more, and unlikely to deteriorate in properties due to the irradiation of light in reproduction.

Among the characteristics in items (1) to (4), those in (1), (2) and (3) are especially important. More specifically, desired recording media are those capable of exhibiting a suitable absorptivity and a high reflectivity on exposure to single semiconductor laser beams for recording and reproducing information. Recording media having a low optical absorptivity require exposure to semiconductor laser beams having a higher recording power. This need represents a marked reduction in service life of the semiconductor laser as well as application of laser beams having a higher recording power, leading to necessity of more labor than needed for the design or maintenance of recording apparatus, so that such recording media are not suited for use. A recording medium having a significantly high optical absorptivity involves a correspondingly low optical reflectivity, resulting in failure to obtain proper signals in reproduction.

While organic dyes are advantageous in being low in toxicity, high in corrosion resistance, inexpensive and fit to densify as compared with the foregoing inorganic materials, the organic dyes with the characteristics (1) and (2) remain to be developed.

An object of the present invention is to provide a cyanine compound suitable for use as a near infrared light-absorbable organic dye which is also useful as a recording medium portion of an optical disk used in combination with a semiconductor laser.

Another object of the invention is to provide a cyanine compound having the characteristics (1) to (4) which are required of near infrared light-absorbable organic dyes useful as the recording medium portion of an optical disk used in combination with a semiconductor laser.

A further object of the invention is to provide a cyanine compound having a reflectivity as high as that of inorganic tellurium-type materials.

A still further object of the invention is to provide a cyanine compound having outstanding solubility in a solvent.

Other features of the invention will become apparent from the following description.

The cyanine compounds of the invention are novel compound undisclosed in literature and represented by the

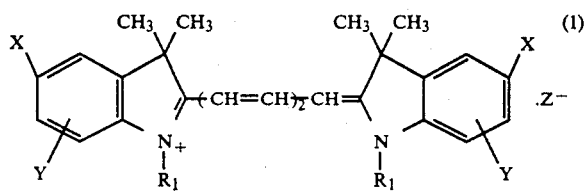

wherein:
X is a lower alkoxy, Y is a lower alkyl or a lower alkoxy, $R_1$ is a lower alkyl, or a lower alkyl substituted with at least one of $C_1$–$C_4$ alkoxy, hydroxy, sulfo, carboxy, $C_1$–$C_4$ alkyl amino, acetoxy, $C_1$–$C_4$ alkoxy carbonyl, $C_1$–$C_4$ sodium sulfonate, $C_1$–$C_4$ sodium carboxylate, alkyl amino methyl, acetoxy methyl, and methoxyl carbonyl methyl, and $Z^-$ is an anion.

Japanese Unexamined Patent Publication No. 85791/1984, and U.S. Pat. Nos. 4,600,625 and 3,916,069 disclose compounds which are similar to the compounds of the present invention and which are represented by the formulae -Compound A-

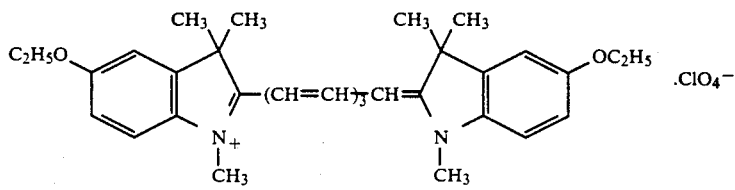

-Compound B-

-continued

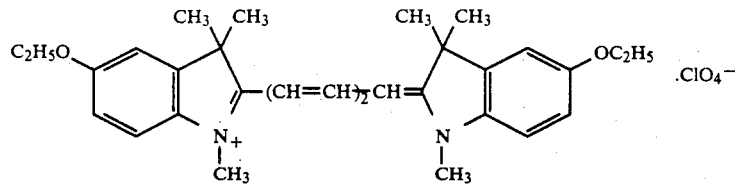

However, the compound A does not exhibit good solubility in solvents and a dye layer formed from the compound A is low in optical reflectivity. The compound B is not satisfactory in solubility in solvents and a dye layer formed from the compound B is very low in optical absorptivity. Consequently, neither the compound A nor the compound B is suitable for use as a near infrared light-absorbable organic dye useful as the recording medium component of an optical disk for use in conjunction with a semiconductor laser.

Shown below are specific examples of the groups represented by X, Y, $R_1$, $R_2$, $R_3$, $R_4$, $R_5$ and Z.

Examples of the lower alkyl group are alkyl groups having 1 to 4 carbon atoms such as methyl, ethyl, n-propyl, isopropyl, n-butyl, isobutyl, tert-butyl and the like.

Examples of the lower alkoxy group are alkoxy groups having 1 to 4 carbon atoms such as methoxy, ethoxy, n-propoxy, isopropoxy, n-butoxy, tert-butoxy and the like.

Examples of the lower alkyl groups represented by $R_1$ in the formula (1) are alkyl groups of 1 to 4 carbon atoms which have at least one substituent selected from the group consisting of $C_4$–$C_4$ alkoxy, hydroxyl, sulfo, carboxy, ($C_1$–$C_4$ alkyl)amino, acetoxy and ($C_1$–$C_4$ alkoxy)carbonyl, such as methoxymethyl, ethoxymethyl, 2methoxyethyl, 2-hydroxyethyl, 2-ethoxyethyl, 2-(n-butoxy)ethyl, n-butoxymethyl, —(CH$_2$)n—SO$_3$Na (wherein n is an integer of 1 to 4), —(CH$_2$)n-COONa (wherein n is an integer of 1 to 4), methylaminomethyl, dimethylaminomethyl, acetoxymethyl, methoxycarbonylmethyl and the like.

Examples of the group Z are halogen, alkyl sulfate residue, arylsulfonate residue, perchlorate residue, tetrafluoroborate residue, arylcarboxylic acid residue and the like. When Z is halogen, examples of $Z^-$ are $Cl^-$, $Br^-$, $I^-$, $F^-$ and the like. When Z is an alkyl sulfate residue, examples of $Z^-$ are $CH_3SO_4^-$, $C_2H_5SO_4^-$, $nC_3H_7SO_4^-$, $n-C_4H_9SO_4^-$ and the like. When Z is an arylsulfonate residue, examples of $Z^-$ are

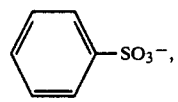

and the like. When Z is a perchlorate residue, examples of $Z^-$ are $ClO_4^-$ and the like. When Z is a tetrafluoroborate residue, examples of $Z^-$ are $BF_4^-$ and the like. When Z is an arylcarboxylic acid residue, examples of $Z^-$ are

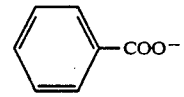

and the like.

Preferable among the compounds according to the invention are those wherein Y is lower alkoxy, $R_1$ is lower alkyl or lower alkoxy-lower alkyl and Z is halogen or perchlorate residue. Preferred compounds further include those wherein Y is substituted at the 6- or 7 position of the indolenine ring, particularly 6-position.

The compound of the formula (1) according to the invention can be prepared by various processes, for example, by the following process which can produce the compound with ease, hence desirable.

The compound of the invention can be prepared by subjecting to condensation reaction an indolenium salt represented by the formula

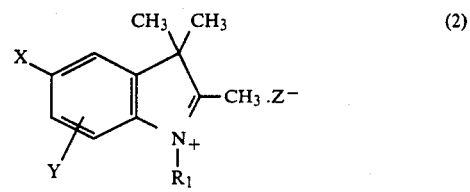

(2)

wherein X, Y, $R_1$ and Z are as defined above and a conventional β-anilino-acrolein-anil hydrochloride represented by the formula

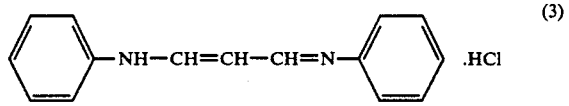

(3)

This condensation reaction is conducted in the presence of a fatty acid salt in an anhydrous organic acid. Examples of useful fatty acid salts are sodium acetate, potassium acetate, calcium acetate, sodium propionate, potassium propionate and the like. The fatty acid salt is used in an amount of about 0.5 to about 3 moles, preferably about 1 to about 2 moles, per mole of the compound of the formula (2). Examples of useful anhydrous organic acids are acetic anhydride, propionic anhydride, butyric anhydride, γ-butyrolactone and the like. The anhydrous organic acid is used in an amount of about 10 to about 100 moles, preferably about 20 to about 50 moles, per mole of the compound of the formula (2). The proportions of compounds of the formulas (2) and (3) are about 0.2 to about 1.5 moles, preferably about 0.4 to about 0.7 mole, of the latter per mole of the former. The reaction smoothly proceeds at a temperature of about 50° to about 150° C., preferably about 100° to about 140° C. and is completed in about 10 to about 60 minutes.

The indolenium salts of the formula (2) include novel compounds undisclosed in literature, and can be prepared, for example, by the following process (in which the compounds (2a) and (2b) are indolenium salts).

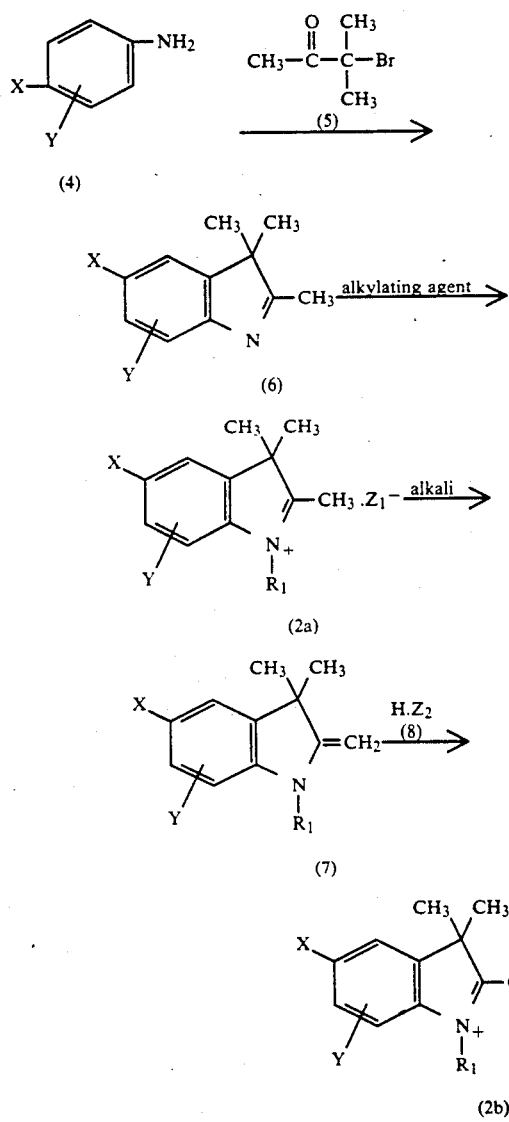

wherein:
Z$_1$ is acidic residue other than perchlorate residue and tetrafluoroborate residue, Z$_2$ is perchlorate residue or tetrafluoroborate residue, and X, Y and R$_1$ are as defined above.

The reaction between the conventional aniline derivative of the formula (4) and the conventional 3-bromo-3-methyl-2-butanone of the formula (5) is performed in the presence of an acid scavenger. Examples of useful acid scavengers are pyridine, triethylamine, tri-n-propylamine, tri-n-butylamine and like tertiary amines, sodium carbonate, potassium carbonate, calcium carbonate and like alkali metal salts of carbonic acids, sodium acetate, potassium acetate, calcium acetate and like alkali metal salts of acetic acids and the like. The acid scavenger is used in an amount of about 0.3 to about 5 moles, preferably about 0.5 to about 1.5 moles, per mole of the compound of the formula (4). The proportions of compounds of the formulas (4) and (5) are about 0.3 mole to about 5 moles, preferably about 0.5 to about 1.5 moles, of the latter per mole of the former. The reaction is conducted at a temperature in the range of from room temperature to about 200° C., preferably from about 50° to about 150° C. and is completed in several hours to about 25 hours, preferably about 5 to about 15 hours.

The compound of the formula (2a) can be prepared by causing an alkylating agent to act on the indolenine derivative of the formula (6) Examples of the alkylating agent which can be used are alkyl toluenesulfonates such as methyl toluenesulfonate, ethyl toluenesulfonate, n-propyl toluenesulfonate, isopropyl toluenesulfonate, n-butyl toluenesulfonate and the like, halogenated alkyls such as ethyl bromide, n-propyl bromide, n-butyl bromide, ethyl iodide, n-propyl iodide, n-propyl chloride, n-butyl chloride and the like, dialkyl sulfates such as dimethyl sulfate, diethyl sulfate and the like. a mixture of acid and epoxy compounds (e.g., a mixture of hydrochloric acid, sulfuric acid or like inorganic acid, acetic acid, propionic acid or like organic acid and ethylene oxide, propylene oxide or the like), etc. The alkylating agent is used in an amount of about 0.3 to about 5 moles, preferably about 0.5 to about 2 moles, per mole of the compound of the formula (6). The reaction is carried out in the absence or in the presence of a solvent. Useful solvents include, for example, toluene, xylene and like alkyl benzenes, n-octane, n-decane, cyclohexane, decalin and like aliphatic hydrocarbons, benzene, naphthalin, tetralin and like aromatic hydrocarbons, trichloroethane, tetrachloroethane, chlorobenzene, dichlorobenzene and like halogenated hydrocarbons, etc. The reaction is conducted at a temperature in the range of from room temperature to about 200° C., preferably from about 50° to about 150° C. and is completed in about 2 to about 30 hours, preferably about 3 to about 15 hours.

The compound of the formula (7) can be prepared by treating the compound (2a) with alkali in a suitable solvent such as water. The alkali to be used can be any of the conventional alkalis such as sodium hydroxide, potassium hydroxide and the like. The amount of alkali used is about 1 to about 20 moles, preferably about 1 to about 5 moles, per mole of the compound (2a). The amount of the solvent used is about 2 to about 100 moles, preferably about 2 to about 20 moles, per mole of the compound (2a). The reaction is conducted at a temperature of 0° to about 150° C., preferably from 0° to about 100° C. and is completed in dozens of minutes to about 10 hours, preferably about 1 to about 5 hours.

The compound (2b) can be prepared by causing compounds of the formula (7) to react with compounds of the formula (8) in the presence of a suitable solvent such as methanol, ethanol, n-propyl alcohol, isopropyl alcohol, n-butanol, isobutyl alcohol, tert-butyl alcohol and like alcohols, benzene, toluene, xylene, n-octane, n-decane, cyclohexane, decalin, trichloroethane, tetrachloroethane, chlorobenzene, dichlorobenzene and like hydrocarbons, etc. The proportions of compounds of the formulas (7) and (8) are about 0.3 to about 10 moles, preferably about 0.5 to about 3 moles, of the latter per mole of the former. The reaction is conducted at a temperature of 0° to about 70° C. and is completed in about 10 minutes to about 3 hours.

The compounds of the invention thus obtained can be easily separated and purified, for example, by column chromatography, recrystallization and the like.

Compounds of the formula (1) according to the invention have a high solubility in an organic solvent such as methanol, ethanol, diacetone alcohol or like alcohols, or dichloromethane, dichloroethane or like aliphatic halogenated hydrocarbons. The compounds have an absorption maximum at about 670 to about 750 nm and have high molar absorptivity. When used as a recording medium feature of an optical disk for use with a semiconductor laser, the compound of the invention shows a high reflectivity of the reading laser light (780 nm) for reproduction, hence is valuable in use.

Given below are a reference example illustrating the preparation of compound of the formula (2) and preparation examples illustrating the preparation of compounds according to the invention.

REFERENCE EXAMPLE

A mixture of 15.36 g of 2,4-dimethoxyaniline, 16.06 g of 3-bromo-3-methyl-2-butanone and 8.0 g of pyridine was reacted at a temperature of 50° to 55° C. for 5 hours. The reaction mixture was further reacted under reflux for 7 hours. After completion of the reaction, the reaction mixture was poured into 70 ml of water and the mixture was extracted with 30 ml of dichloromethane. The solvent was distilled off and the residue was subjected to vacuum distillation, giving 12.0 g of 2,3,3-trimethyl-5,7-dimethoxyindolenine having a boiling point of 125 to 130° C./2-3mmHg.

A mixture of 10.96 g of 2,3,3-trimethyl-5,7-dimethoxyindolenine obtained above, 11.00 g of ethyl p-toluenesulfonate and 60 ml of toluene was reacted under reflux for 8 hours. The reaction mixture was subjected to extraction with 50 ml of water, giving 1-ethyl-2,3,3-trimethyl-5,7-dimethoxyindolenium.toluenesulfonate.

To the extract was added 20 g of 20% NaOH, and the mixture was reacted at 70° C. for 3 hours. The reaction mixture was submitted to extraction with 30 ml of toluene. The toluene was distilled off and the residue was subjected to vacuum distillation, giving 6.00 g of 1-ethyl-2-methylene-3,3-dimethyl-5,7-dimethoxyindoline with a boiling point of 122° to 129° C./3-4mmHg.

A 2.87 g quantity of 70% HClO$_4$ was added to a mixture of 4.95 g of 1-ethyl-2-methylene-3,3-dimethyl-5,7-dimethoxyindoline and 60 ml of isopropanol at not higher than 20° C. The mixture was stirred at room temperature for 1 hour and cooled to not higher than 5° C. The deposited crystals were filtered off, washed with isopropanol and dried, giving 6.54 g of 1-ethyl-2,3,3-trimethyl-5,7-dimethoxyindolenium.perchlorate with a melting point of 222.5° to 226.5° C.

PREPARATION EXAMPLE 1

A 4.21 g quantity of compound of the formula (1) (wherein X=methoxy, Y=methoxy (7-position of the indolenine ring, the same hereinafter), R$_1$=ethyl, Z$^-$=ClO$_4^-$) was produced by repeating the same procedure as in Preparation Example 1 using 5.22 g of compound of the formula (2) (wherein X=methoxy, Y=methoxy (7-position), R$_1$=ethyl, Z$^-$=ClO$_4^-$).

Melting point: 250°-252° C.
λmax: 693 nm alcohol).
ε: 1.84×10$^5$cm$^{-1}$.

PREPARATION EXAMPLE 2

The compound of the formula (1) (wherein X=ethoxy, Y=ethoxy (7-position), R$_1$=ethyl, Z$^-$=ClO$_4^-$) was produced by repeating the same procedure as in Preparation Example 1 using the compound of the formula (2) (wherein X=ethoxy, Y=ethoxy (7-position), R$_1$=ethyl, Z$^-$=ClO$_4^-$).

λmax: 698 nm (dichloromethane).
ε: 1.72×10$^5$cm$^-$.

Compounds were produced in Preparation Examples 3 to 14 by repeating the same procedure as in Preparation Example 1 using a suitable class of compound of the formula (2).

PREPARATION EXAMPLE 3

Compound of the formula (1) (X=methoxy, Y=methoxy (6-position), R$_1$=methoxymethyl,

λmax: 702 nm (diacetone alcohol)
ε: 1.60×10$^5$cm$^{-1}$

PREPARATION EXAMPLE 4

Compound of the formula (1) (X=methoxy, Y=methyl (7-position), R$_1$=2-hydroxyethyl, Z$^-$=ClO$_4^-$)
λmax: 679 nm (diacetone alcohol)
ε: 1.84×10$^5$cm$^{-1}$

PREPARATION EXAMPLE 5

Compound of the formula (1) (X=methoxy, Y=methyl (7-position), R$_1$=2-methoxyethyl, Z$^-$=ClO$_4^-$)
λmax: 679 nm (diacetone alcohol)
ε: 1.85×10$^5$cm$^{-1}$

PREPARATION EXAMPLE 6

Compound of the formula (1) (X=methoxy, Y=methyl (6-position), R$_1$=n-propyl, Z$^-$=I$^-$)
λmax:683 nm (diacetone alcohol)
ε: 1.74×10$^5$cm$^{-1}$

PREPARATION EXAMPLE 7

Compound of the formula (1) (X=ethoxy, Y=methyl (7-position), R$_1$=ethyl, Z$^-$=BF$_4^-$)
λmax: 681 nm (dichloroethane)
ε:1.75×10$^5$cm$^-$

PREPARATION EXAMPLE 8

Compound of the formula (1) (X=n-propoxy, Y=methyl (7-position), R$_1$=ethyl, Z$^-$=ClO$_4^-$)
λmax: 683 nm (diacetone alcohol)
:ε1.63×10$^5$cm$^{-1}$

PREPARATION EXAMPLE 9

Compound of the formula (1) (X=methoxy, Y=ethyl (7-position), R$_1$=ethyl, Z$^-$=ClO$_4^-$)
λmax: 681 nm (diacetone alcohol)
δ: 1.82×10$^5$cm$^{-1}$

PREPARATION EXAMPLE 10

Compound of the formula (1) (X=methoxy, Y=isopropyl (7-position), R$_1$=methyl, Z$^-$=I$^-$)
λmax: 681 nm (diacetone alcohol)
ε: 1.62×10$^5$cm$^{-1}$

PREPARATION EXAMPLE 11

Compound of the formula (1) (X=methoxy, Y=methoxy (6-position), R$_1$=n-butyl, Z$^-$=I$^-$)
λmax: 703 nm (diacetone alcohol)

ε: $1.62 \times 10^5$ cm$^{-1}$

PREPARATION EXAMPLE 12

Compound of the formula (1) (X=methoxy, Y=methoxy (6-position), $R_1$=n-buthyl, $Z^-=ClO_4^-$)
λmax: 699 nm (dichloromethane)
ε: $1.61 \times 10^5$ cm$^{-1}$

PREPARATION EXAMPLE 13

Compound of the formula (1) (X=methoxy, Y=methoxy (7-position), $R_1$=acetoxyethyl, $Z^-=ClO_4^{31}$)
max: 693 nm (diacetone alcohol)
ε: $1.75 \times 10^5$ cm$^{-1}$

PREPARATION EXAMPLE 14

Compound of the formula (1) (X=methoxy, Y=methoxy (7-position), $R_1$=methoxyethyl, $Z^-=I^-$)
λmax: 695 nm (diacetone alcohol)
ε: $1.80 \times 10^5$ cm$^{-1}$

TEST FOR REFLECTIVITY AND ABSORPTIVITY

Each of cyanine dyes as shown below in Table 1 was dissolved in dichloromethane to a concentration of 20 g/l. The solution was applied to an acrylic resin plate by a spin coater rotated at 1500 rpm to form a layer of 600 to 700 Å thickness, and the coating was dried. The reflectivity and absorptivity of the coating were measured by irradiation of semiconductor laser beam at 780 nm over the coating surface. Table 1 below shows the results.

TEST FOR OPTIMUM RECORDING POWER

Information was recorded on a photosensitive recording medium formed using each of the cyanine dyes shown below in Table 1 by irradiation of semiconductor laser beams at 780 nm at a recording power of 0.2 mW, a liner velocity of 1.2 m/s and a frequency of 450 kHz and the recorded information was reproduced at a reproducing power of 0.2 mW. The optimum recording power is one at which errors occur at the lowest frequency (CN ratio of at least 45 dB and error rate of up to 50 cps) when the recording is reproduced at varying recording powers of from 2.0 to 8.0 mW and the recorded information was reproduced by irradiation of semiconductor laser beams at 780 nm at a reproducing power of 0.2 mW.

TABLE 1

| Cyanine dye | Reflectivity (%) | Absorptivity (%) | Optimum recording power (mW) |
| --- | --- | --- | --- |
| Dye of Prep. Ex. 1 | 42 | 19 | 2.7 |

TABLE 1-continued

| Cyanine dye | Reflectivity (%) | Absorptivity (%) | Optimum recording power (mW) |
| --- | --- | --- | --- |
| Dye of Prep. Ex. 3 | 41 | 18 | 2.8 |
| Dye of Prep. Ex. 6 | 40 | 13 | 3.0 |
| Dye of Prep. Ex. 11 | 40 | 18 | 2.8 |
| Dye of Prep. Ex. 12 | 41 | 19 | 2.6 |
| Dye of Prep. Ex. 14 | 41 | 18 | 2.6 |
| Compound A | 24 | 58 | 3.6 |
| Compound B | 40 | 7 | at least 6.0 |

TEST FOR SOLUBILITY IN SOLVENT

Each of cyanine dyes as shown below in Table 2 was dissolved in methanol and the solubility was determined at room temperature with the results indicated below in Table 2.

TABLE 2

| Cyanine dye | Solubility (g/l) |
| --- | --- |
| Dye of Prep. Ex. 1 | 30 |
| Dye of Prep. Ex. 3 | at least 30 |
| Dye of Prep. Ex. 6 | at least 30 |
| Dye of Prep. Ex. 11 | at least 30 |
| Dye of Prep. Ex. 14 | at least 30 |
| Compound A | up to 10 |
| Compound B | up to 10 |

We claim:

1. A cyanine compound represented by the formula

[Structure of formula (1): indolenine-based cyanine dye with substituents X, Y, $R_1$, and counterion $Z^-$, linked by $-(CH=CH)_2-CH=$ chain]

wherein:
X is a lower alkoxy, Y is a lower alkyl or a lower alkoxy, $R_1$ is a lower alkyl, or a lower alkyl substituted with at least one of $C_1$-$C_4$ alkoxy, hydroxy, sulfo, carboxy, $C_1$-$C_4$ alkyl amino, acetoxy, $C_1$-$C_4$ alkoxy carbonyl, $C_1$-$C_4$ sodium sulfonate, $C_1$-$C_4$ sodium carboxylate, alkyl amino methyl, acetoxy methyl, and methoxyl carbonyl methyl, and $Z^-$ is an anion.

2. A compound according to claim 1 wherein $Z^-$ is halide or perchlorate.

3. A compound according to claim 2 wherein Y is lower alkoxy.

4. A compound according to claim 3 wherein Y is substituted at the 6- or the 7-position of the indolenine ring.

5. A compound according to claim 4 wherein $R_1$ is lower alkyl or lower alkoxy-lower alkyl.

* * * * *